(12) United States Patent
Mayda, II et al.

(10) Patent No.: US 7,490,722 B2
(45) Date of Patent: Feb. 17, 2009

(54) ENDOBIN

(76) Inventors: Jaro Mayda, II, 3611 S. Reed Rd., #105, Kokomo, IN (US) 46902; Kent DeBoer, 2000 Beach St., #306, San Francisco, CA (US) 94123

( * ) Notice: Subject to any disclaimer, the term of this patent is extended or adjusted under 35 U.S.C. 154(b) by 695 days.

(21) Appl. No.: 11/132,099

(22) Filed: May 18, 2005

(65) Prior Publication Data

US 2006/0260968 A1    Nov. 23, 2006

(51) Int. Cl.
*B65D 83/10* (2006.01)
(52) U.S. Cl. ............... 206/364; 206/438; 206/499; 206/503
(58) Field of Classification Search .......... 206/303, 206/438, 363–366, 571, 409, 389, 394, 210, 206/391, 499, 503, 505–507, 514, 558; 211/163, 211/144, 126.2, 57.1, 131.1, 129.1, 56; 312/249.2; 220/23.83, 23.86, 505; 222/129, 132, 143, 222/144; 242/588, 588.3, 588.6, 579, 580, 242/129
See application file for complete search history.

(56) References Cited

U.S. PATENT DOCUMENTS

| | | | |
|---|---|---|---|
| 4,936,448 A | 6/1990 | Holloway |
| 5,372,254 A | 12/1994 | Gross |
| 5,392,918 A | 2/1995 | Harrison |
| 5,611,428 A | 3/1997 | Banerian |
| 5,738,213 A | 4/1998 | Whiting |
| 5,769,222 A | 6/1998 | Banerian |
| 5,947,284 A | 9/1999 | Foster |
| 6,047,825 A | 4/2000 | Samuels |
| 6,053,313 A | 4/2000 | Farrell |
| 6,068,121 A | 5/2000 | McGlinch |
| 6,375,006 B1 | 4/2002 | Samuels |
| 6,547,072 B2 | 4/2003 | Whiting |
| 6,719,135 B2 | 4/2004 | Armijo |

*Primary Examiner*—Mickey Yu
*Assistant Examiner*—Steven A. Reynolds
(74) *Attorney, Agent, or Firm*—Frank D. Lachenmaier

(57) ABSTRACT

This invention relates generally to a unique device in which the several guide wires for catheters or other interventional devices used in a typical endovascular procedure for diagnostics or other purposes are temporarily stored and presented to surgical team and in which the used devices and collected bodily fluids are securely disposed of after sealing lid is attached.

6 Claims, 6 Drawing Sheets

Figure 1:
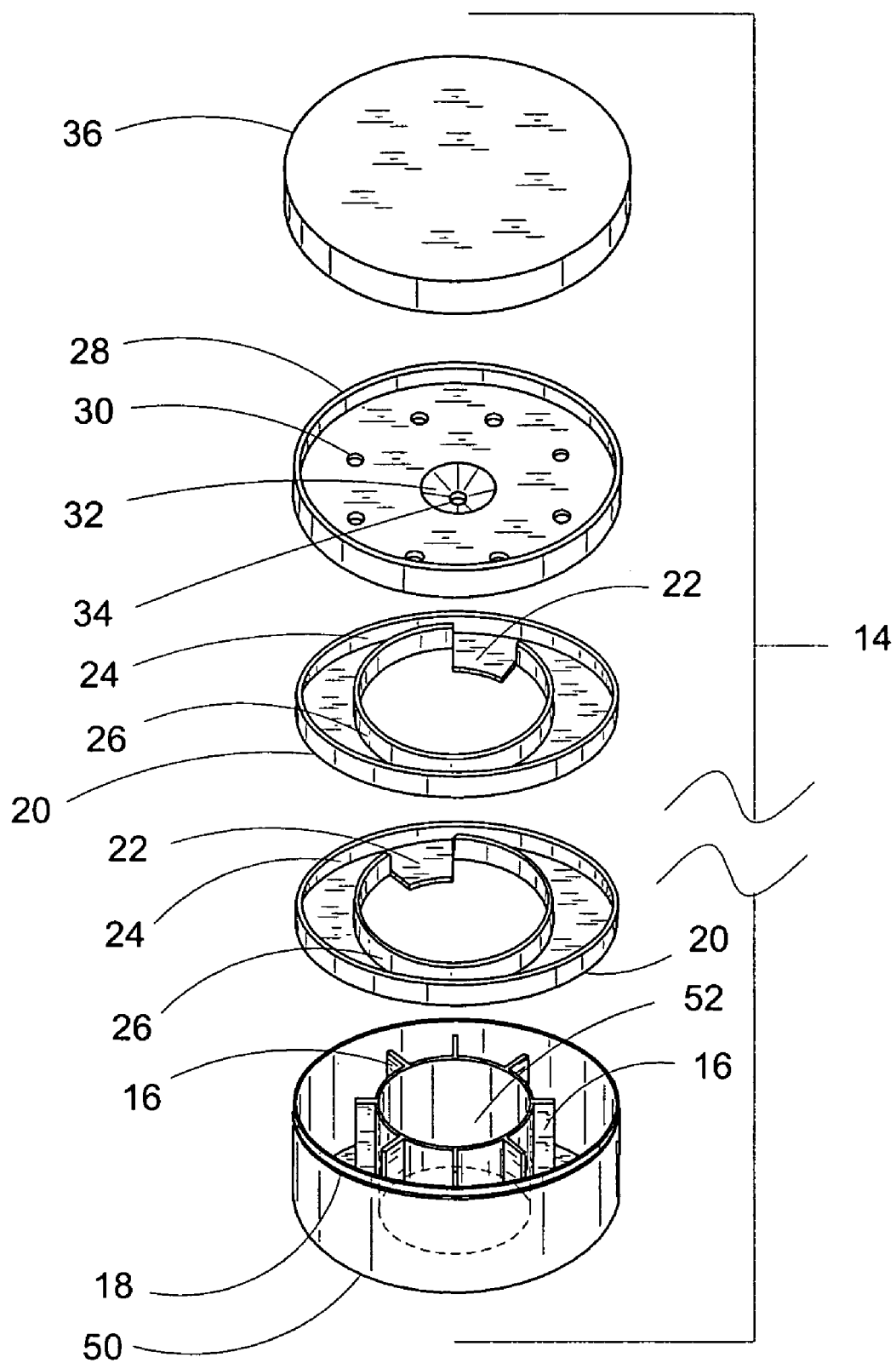

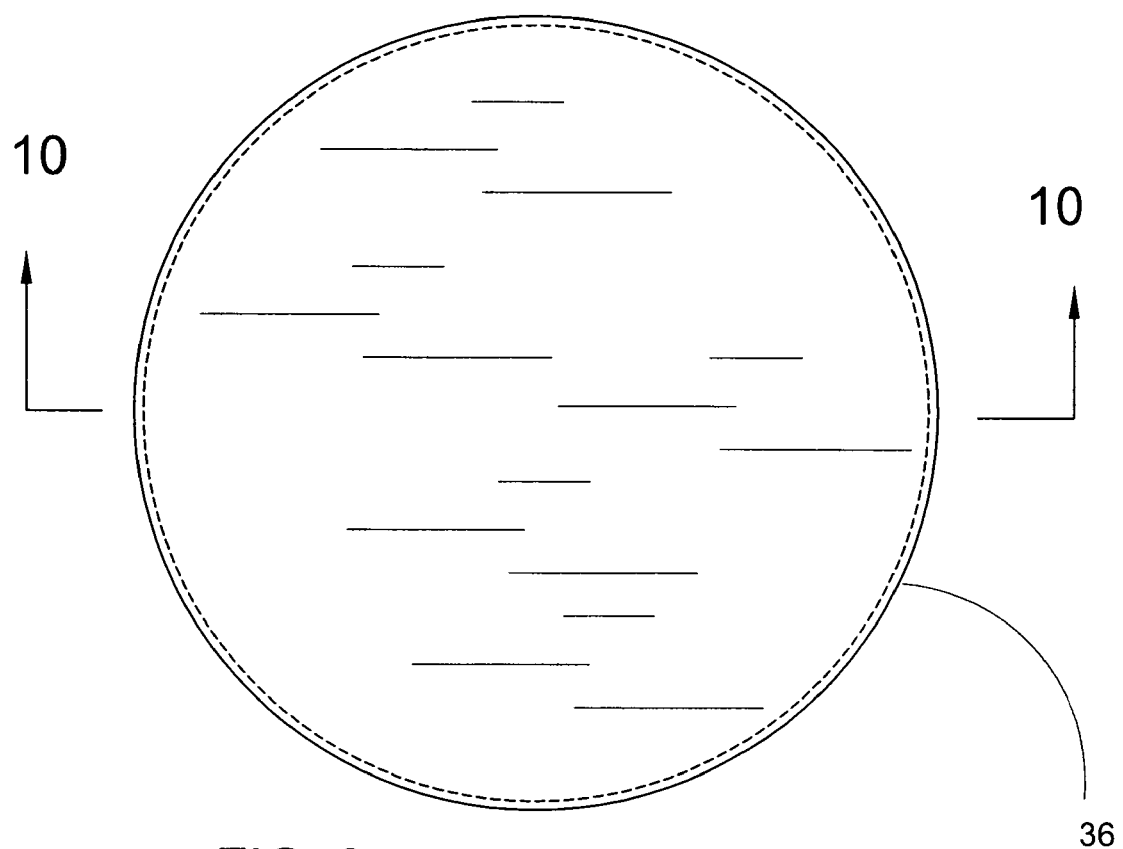
FIG. 9
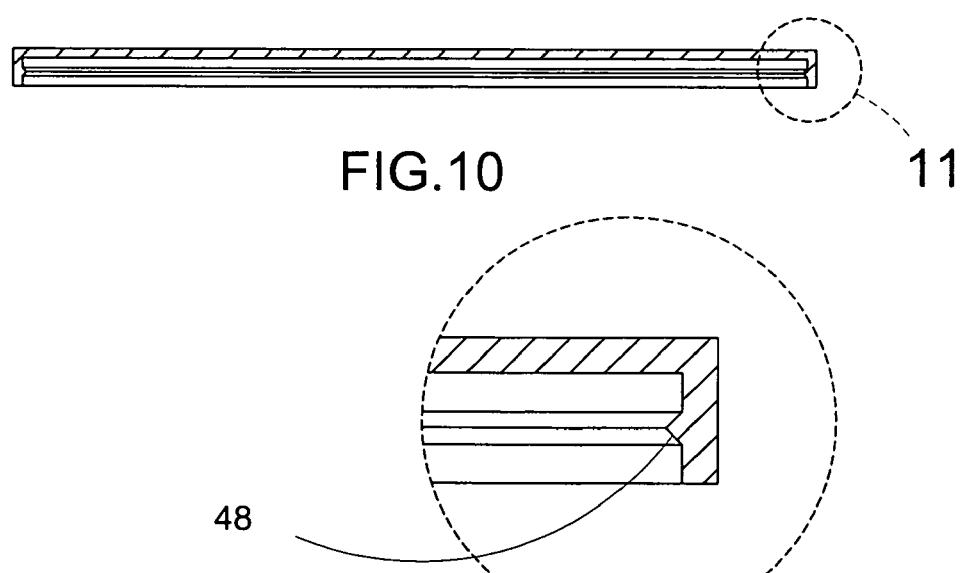
FIG.10
FIG.11

ENDOBIN

BACKGROUND

1. Field of Invention

This invention relates generally to a unique device in which the several guide wires for catheters or other interventional devices used in a typical endovascular procedure for diagnostics or other purposes are presented, stored and disposed of in a secure, ordered and easily accessible manner.

2. Prior Art

Guide wires of different diameters, lengths, materials and construction may be used in the same procedure. These wires are typically delivered to the operating room in sterile bags in a coiled form and start at approximately 75 cm. in length. They are removed from the bags and inserted into a patient's body into a tubular structure of interest. The external portion is coiled by hand and typically stored under a sterile towel or placed in a bowl filled with a saline solution. Once a guide wire is in place, a balloon catheter, stent or atherectomy device may be sent along the wire and the wire removed and later reused for another stenosis or sight of interest or it may be advanced further into the patient. These wires are difficult to handle while avoiding contact with non-sterile surfaces. It is not easy for a physician to select the desired wire or catheter for the procedure if several are stored together and tangling of adjacent wires is also a problem. If a wire should uncoil unexpectedly a chance for contact with a non-sterile surface occurs. Open bowls filled with various wires are not very stable. A device which attempts to provide an ordered storage of wire catheter devices during an endovascular procedure was described in U.S. Pat. No. 6,047,825 Samuels 2000 wherein a long tube which can be coiled or elongated with a funnel type opening on one end and a slotted cover for the funnel end is disclosed. The various catheters are inserted through the various slots which separate the ends of the catheters but do not keep them isolated from each other and in a sterile environment. A ring or collar can be placed around the base or the face of the funnel such that it is held in an elevated attitude keeping fluids in the elongated tube from escaping. The most significant problem with these type storage devices is that the various catheters are all enclosed within the same tube and cross contamination or tangling is not only possible but likely. The described device also is not very stable and spills in use or post procedure handling are possible.

SUMMARY

An object of the present invention is to provide a stable temporary storage platform for catheters, guide wires, stents and other such devices used during the course of an interventional or diagnostic procedure.

Another object of the present invention is to provide a secure method of disposal of catheters, stents, guidewires and other such devices.

A further object is to provide a secure method for disposal of contaminated body fluids collected during a procedure.

A further object is to provide an ordered storage platform that keeps the devices from touching each other, thus eliminating the tangling problem and the separate device locations can be labeled for easy identification and retrieval.

DRAWINGS

Figure 2:
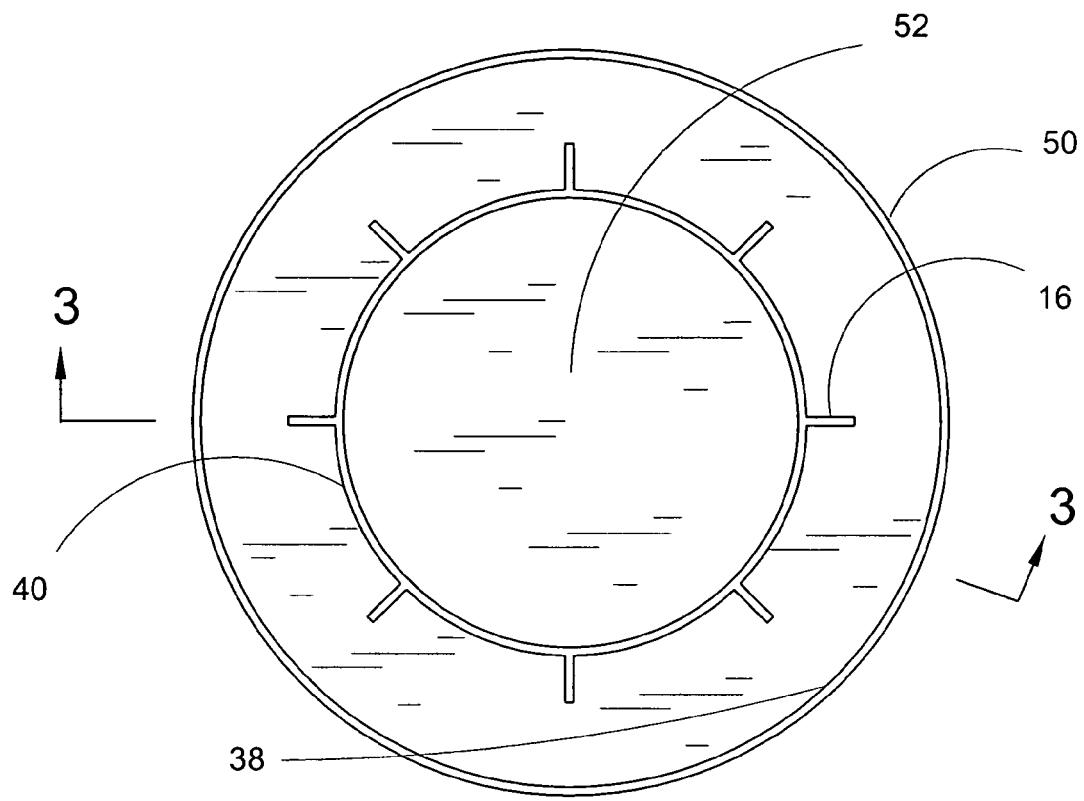
Figure 3:
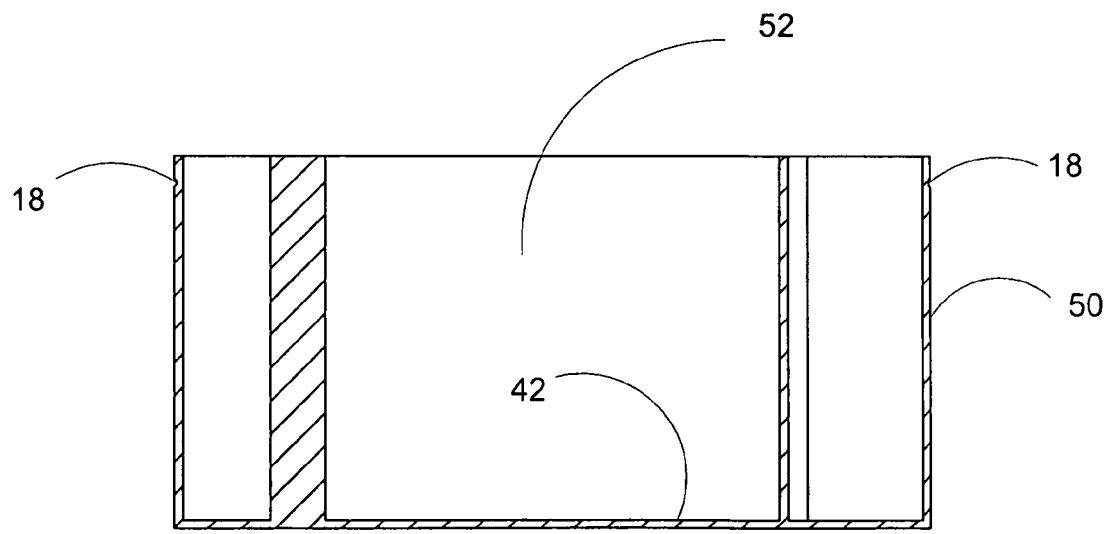
Figure 4:
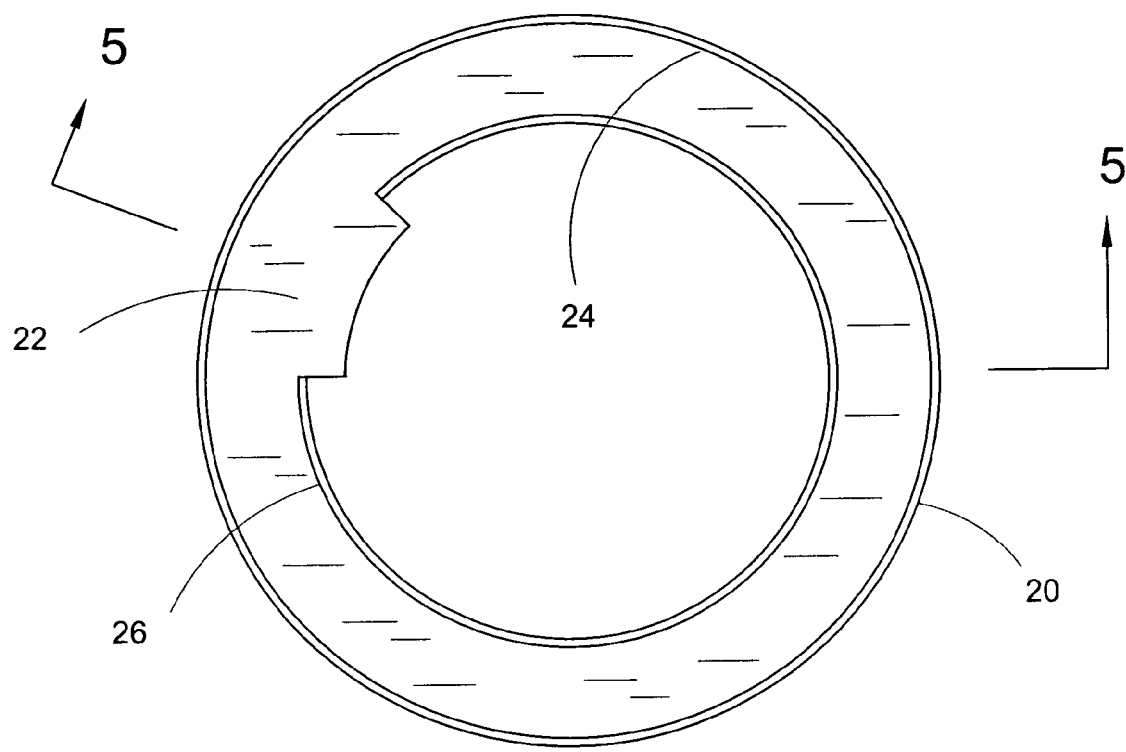
Figure 5:
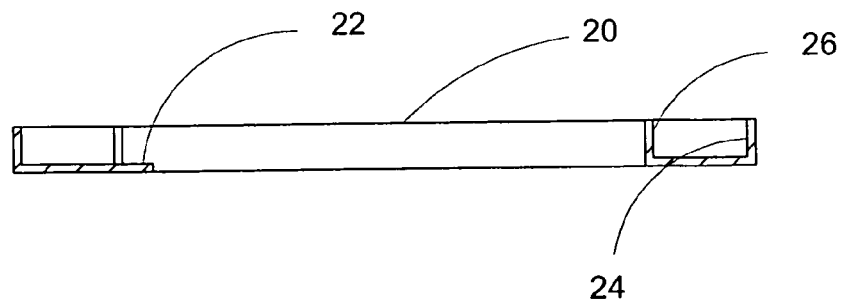
Figure 6:
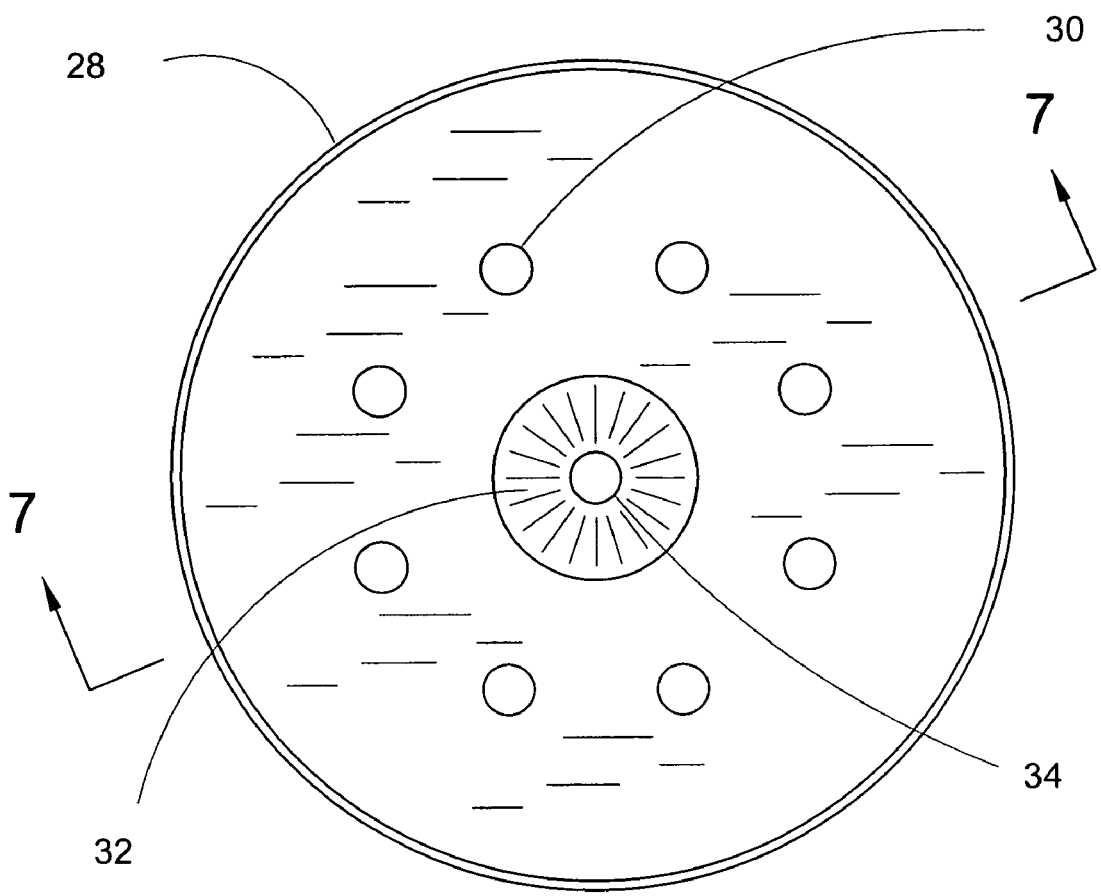
Figure 7:
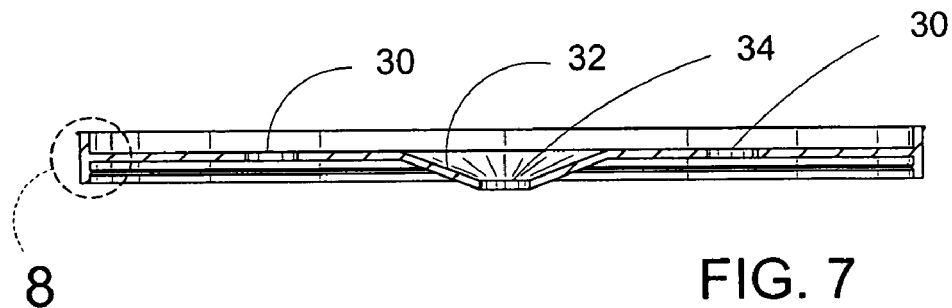
Figure 8:
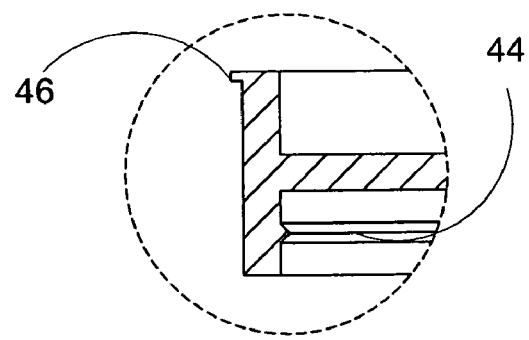
Figure 12:
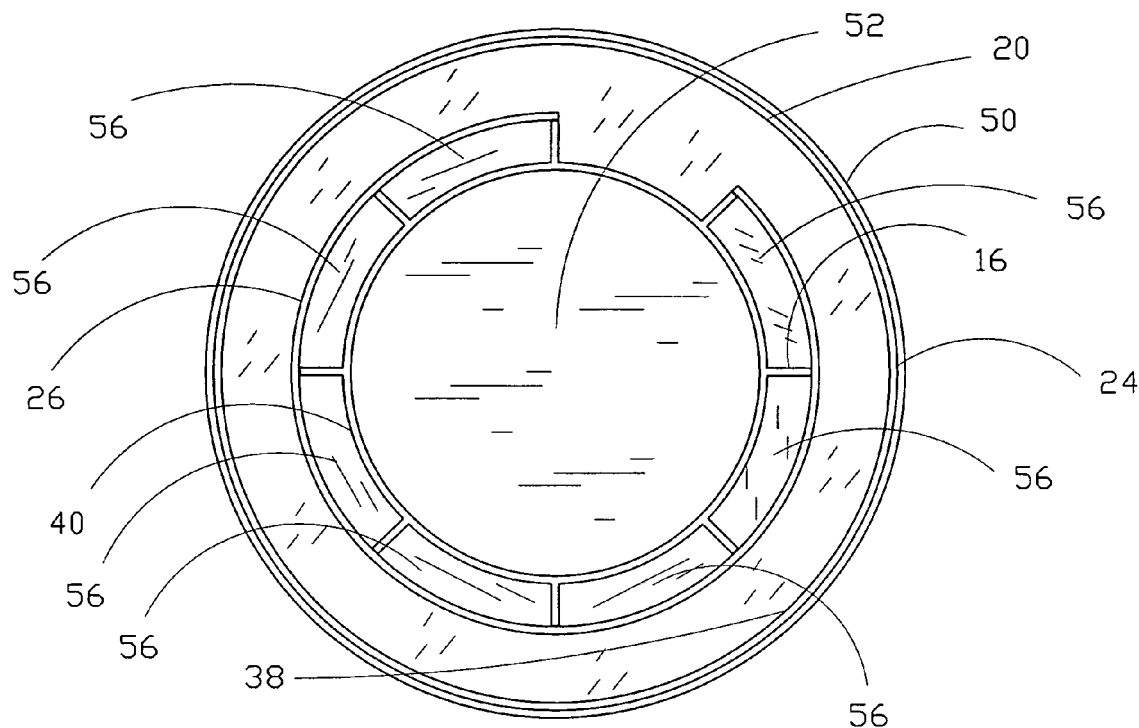
Figure 13:
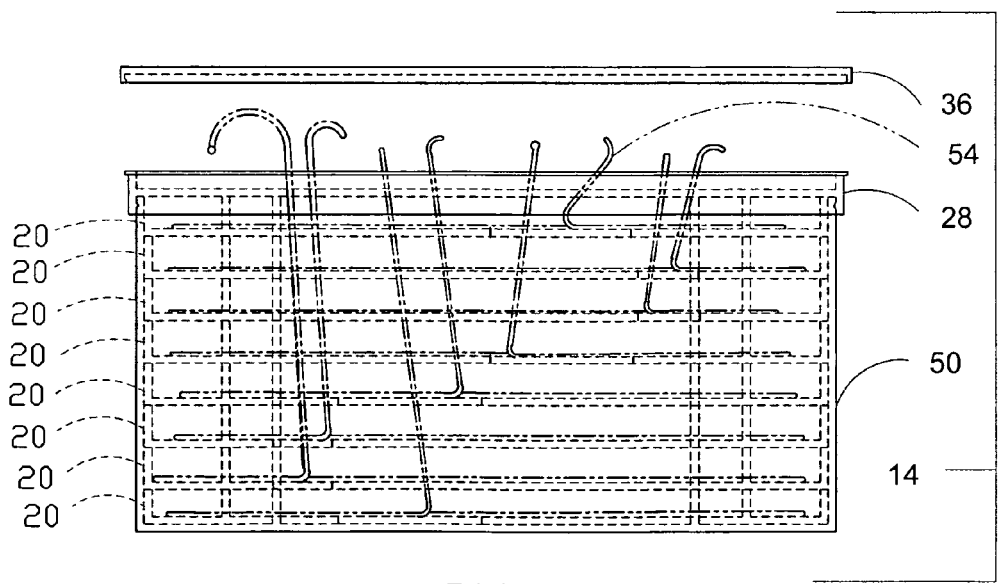

In order that Endobin may be more fully understood it will now be described by way of example, with reference to the accompanying exemplary drawings in which:

FIG. 1 is a partial exploded perspective view of an Endobin assembly showing only two of the eight baffles.
FIG. 2 is a top view of base 50.
FIG. 3 is a section view of base 50.
FIG. 4 is a top view of baffle 20.
FIG. 5 is a section view of baffle 20.
FIG. 6 is a top view of top plate 28.
FIG. 7 is a section view of top plate 28.
FIG. 8 is a 4× partial sectional view of top plate 28.
FIG. 9 is a top view of lid 36.
FIG. 10 is a section view of lid 36 cut along section lines 10-10.
FIG. 11 is a 4× partial sectional view of lid 36.
FIG. 12 is a top view of base 50 with eight baffles 20 inserted.
FIG. 13 is a partially exploded side view of an Endobin. Catheters and wires, shown here in phantom lines, are for illustrative purposes only and form no part of this invention.

REFERENCE NUMERALS

The same reference numbers are used to refer to the same or similar parts.
- 14—Endobin assembly
- 16—flange
- 18—detent groove
- 20—baffle
- 22—inward extension
- 24—exterior upstanding baffle rim
- 26—interior upstanding baffle rim
- 28—top plate
- 30—bin access holes
- 32—center funnel
- 34—reservoir access hole
- 36—lid
- 38—interior base wall
- 40—exterior reservoir wall
- 42—reservoir bottom
- 44—top plate to base detent
- 46—top plate to lid detent
- 48—lid to top plate retainer ring
- 50—base
- 52—reservoir
- 54—wires and catheters shown in phantom lines not part of this invention
- 56—access pocket

DESCRIPTION

The present invention, in its several embodiments, meets the above mentioned objectives.

An object of the present invention is to provide a stable temporary storage platform for catheters, guide wires, stents and other such devices 54 used during the course of an interventional procedure. This is accomplished by molding base 50 with a ratio of diameter to height of approximately 2:1. In the preferred embodiment, Endobin 14 is approximately 20.3 cm. in diameter and 10.1 cm. tall.

Another object of the present invention is to provide a secure method of disposal of catheters, stents, guidewires and other such devices 54. When the procedure is completed the various devices can be completely inserted through access holes 30 in top plate 28 and lid 36 snapped in place making a neatly disposable package.

A further object is to provide a secure method for disposal of contaminated body fluids collected during a procedure. The center of Endobin 14 is a well or reservoir for discarded body fluids that are captured by the center funnel 32 and guided into reservoir 52 by way of reservoir access hole 34. Again snapping lid 36 onto top plate 28 seals Endobin 14 assembly and makes it a safe package for disposal.

A further object is to provide an ordered storage platform that keeps the devices 54 from touching each other, thus eliminating the tangling problem. Each wire 54 is coiled on it own separate level, entered through its own access hole 30 and access pocket 56 and separated by the plurality of baffles 20. The separate device access holes 30 can be labeled for easy identification and retrieval of the stored devices 54 protruding from them.

DESCRIPTION OF THE PREFERRED EMBODIMENTS

FIG. 1 shows an exploded perspective view of an Endobin 14 with a break in the view between a bottom baffle 20 and a top baffle 20. For the preferred embodiment there are 8 baffles 20 that are dropped into base 50, rotating 45 degrees between each successive baffle, fitting inward extension 22 between flanges 16 and against exterior reservoir wall 40. This assembly creates access pockets 56 bottomed by inward extension 22 of each baffle, open to the top plate 28 which has matching access holes 30 aligned over access pockets 56. This view also shows lid 36 which, when snapped over top plate 28, makes a sealed package for disposal.

FIG. 2 shows a top view of base 50. In the preferred embodiment of Endobin 14, the base is comprised of an approximately 20.3 cm. diameter by 10.1 cm. tall cylinder open at the top and closed at the bottom with a concentric 12.7 cm. diameter interior reservoir 52 also open at the top and closed at the bottom and approximately 10.1 cm. tall. The exterior reservoir wall 40 has radial flanges the full height, protruding outward approximately 12.7 mm., spaced around the perimeter at 45 degree intervals. Base 50 can be molded from any of the engineering thermoplastics as it will not be a sterilization vehicle and won't be subjected to temperature or humidity extremes. Flexibility and lubricity are important properties to aid in the snap together assembly of top plate 28 to base 50 and lid 36 to top plate 28. Wall thickness in the preferred embodiment is approximately 2.4 mm. A detent groove on the outside wall of base 50, approximately 4.8 mm. below the top of said wall, provides the detent snap location for bump 44 in top plate 28.

FIG. 3 shows the side walls and bottom 42, plus the reservoir walls and one of the radial fins 16 of base 50 in a section view.

Turning to FIG. 4 we have a top view of baffle 20. This baffle 20 is also molded of an engineering thermoplastic and is comprised of an annular ring with approximately 12.7 mm. upstanding walls 24 and 26, with an internal diameter of approximately 15.24 cm. that allows for slipping over flanges 16 and an external diameter small enough to allow for an easy slip fit into base 50. The internal upstanding wall 26 is broken for an approximate 45 degree section and inward extension 22 of the bottom wall of baffle 20 is angled inward approximately 12.7 mm. such that it rests against exterior reservoir wall 40 and between right and left flanges 16. Wall thicknesses are again approximately 2.4 mm.

FIG. 5 is a cross section showing inward extension 22 and upstanding rims 24 and 26.

FIG. 6 is a top view of top plate 28 disclosing an approximately 20.3 cm. diameter disc approximately 2.4 mm. thick, with perimeter walls extending above and below the disc approximately 5.2 mm. The top surface of the disc has eight access holes 30 approximately 12.7 mm in diameter on approximately 14 cm. diameter centers, equally spaced at approximately 45 degree intervals. The center of the disc has an approximate 5.1 cm. diameter funnel 32 opening downward to a 12.7 mm. diameter reservoir access hole 34 approximately 2.4 mm. below the bottom of the distending wall as shown in FIG. 7. FIG. 8 shows a retaining ring 44 for snapping top plate 28 into detent groove 18 on base 50 midway down the inside of the distending wall. Around the outside perimeter at the top of the upstanding wall is detent bump 46 for snapping into lid to top retainer snap 48.

FIG. 9 shows an approximately 20.3 cm. diameter lid 36 sufficiently larger than top plate 28 to allow for snap fitting over top plate 28. FIG. 10 shows a cross section of lid 36 with its approximate 2.4 mm. wall thickness and 9.6 mm. height. FIG. 11 is a 4× partial blowup view of lid 36 to illustrate its top retainer snap 48 details. Lid 36 snapped over top plate 28 which is snapped onto base 50 makes this a liquid tight disposable case for used devices 54 and contaminated body fluids trapped in reservoir 52.

FIG. 12 shows a top view of eight baffles 20 stacked inside base 50 with each baffle 20 progressively rotated 45 degrees before stacking. Inward extension 22 forms a bottom of access pocket 56 which is bounded by exterior reservoir wall 40, right and left flanges 16, and interior upstanding baffle rims 26 of eight baffles 20, allowing access to each level though access holes 30 in top plate 28 aligned above access pockets 56.

FIG. 13 shows catheters or wires 54, shown in phantom lines and not part of this invention, are inserted through access holes 30 down into Endobin 14 until they hit inward extension 22 at the bottom of access pocket 56. Wire 54 is then turned outward and moved circumferentially around baffle 20 between interior and exterior upstanding rims 26 and 24 respectively, until as much as needed is enclosed within Endobin 14. Access holes 30 are labeled to make selection of the appropriate device 54 easier and the devices 54 each having their own level will not tangle. The devices 54 should also be much less likely to touch a non-sterile surface. The diameter to height ratio of 2:1 makes the Endobin 14 very stable. Its stability can be improved even further by adding water to the interior reservoir 52. If bodily fluids do run down device 54 wires and get on top plate 28 they will be directed into the reservoir 52 by the sloping surface of funnel 32 through reservoir access hole 34.

When the procedure is completed, wires or catheters 54 are shoved through the access holes 30 and lid 36 is snapped into place making a secure, disposable package.

Operation of the Preferred Embodiments:

An Endobin 14 apparatus is positioned in close proximity to a patient that is ready to undergo an endovascular procedure. The catheters, guidewires and other such devices 54 used in such a procedure are typically presented in coiled form in sterile bags with twist wires to prevent uncoiling into their natural straight wire shape. The devices are removed from their plastic bags and ties and the proximal ends are fed though access holes 30 in top plate 28, down though access pockets 56 until they contact inward extension 22 of bottom wall of a baffle 20. The device is then rotated outward though a break in the upstanding interior side wall 26 of baffle 20 and into a channel or bin formed by the interior and exterior upstanding walls 24 and 26, the bottom wall of baffle 20 and the bottom wall of the next baffle 20 up in the stack. Once the proximal end of device 54 is started into the channel it is fed circumferentially around the channel until only the distal end of the device is protruding above top plate 28 far enough to be easily grasped by attending physician. Wire devices 54 are inserted into a tubular member inside a patient's body and fed along the member until it reaches the point of interest or action. Once an action is completed the device 54 may be further advanced into the member, partially retracted or completely removed from the body, sometimes to be reused later in the procedure other times to be disposed of. It is not uncommon for some bodily fluids to leak from the body during the procedure and run along the wires 54. Top plate 28 is sloped downward towards a reservoir access hole 34 at its center to allow for collection of such waste fluids into impermeable reservoir 52 for later disposal.

When the procedure is completed the distal ends of devices 54 are pushed completely to the top surface of top plate 28 and sealing lid 36 is attached over top plate 28 securely and the whole Endobin 14 unit is disposed of without danger to the disposing personnel.

The description of the Endobin 14 above is not intended to limit this invention to an eight device storage system. Scaling in both size and plurality of devices to be stored or used in a given procedure can be easily understood by someone of ordinary skill in these arts. Although the preferred embodiment is described with the component parts injection molded from an engineering grade of thermoplastic it is not so limited and several or all of the components could be constructed from other materials and techniques familiar to those of ordinary skill in these fabrication arts.

What is claimed is:

1. An apparatus for presenting and storing medical guide wires, catheters, stents, and other such delivery platform devices during interventional or diagnostic endovascular procedures and disposing of waste bodily fluids collected and said devices used during said procedure comprising:
  a) a base of generally cylindrical shape having a closed bottom, an open top, an inside wall, an outside wall, an internal cylindrical reservoir that is co-axial with and annular to said base, with a plurality of outward extending flanges equally spaced about said reservoir's outside wall perimeter, extending from the bottom to the top of said reservoir's outside wall;
  b) a plurality of baffles that stack inside said base between said base internal wall and the outside edges of said flanges after each of said plurality of baffles is rotated or indexed by one position for each successive baffle, where said baffles are annular rings with upstanding external and internal baffle walls connected with a bottom baffle wall, wherein said internal upstanding wall is broken for a sufficient angle to allow said bottom wall to extend inward between one set of said flanges until it contacts said outside wall of said reservoir making a bottom for an access pocket at each of said baffle levels where said access pocket is bounded by said inward extension of said bottom baffle wall, right and left sides walls by said flanges, said outside wall of said reservoir and said upstanding internal walls of above stacked baffles and open from bottom side of a top plate through said broken upstanding internal baffle wall into an annular channel or bin;
  c) a circular top plate with upstanding and distending perimeter walls, a plurality of access holes which are centered over each of said access pockets, wherein said guidewire and other such devices can be stored by being inserted through said access holes, fed down through said access pockets to said pocket bottoms, turned outward through said break in internal upstanding baffle wall and fed circumferentially around said channel formed by said baffle's upstanding walls, bottom and the bottom of the above baffle in said stack or withdrawn fully or partially, used and returned without danger of tangling or contamination since said devices are isolated in their own bin level, a center section which slopes downward toward the center where it joins a reservoir access hole directly above said reservoir to capture runoff of bodily fluids;
  d) a sealing lid with a distending perimeter wall that can be attached to said top plate at the end of said procedure after said disposable devices are fully inserted into their bins and said waste fluids have been collected in said reservoir, making a sealed disposable package with no danger of spills or accidental exposure of disposal personnel to said waste fluids or coiled devices.

2. The apparatus of claim 1 wherein said base, top plate and lid have snap together assembly means and are constructed from a material impermeable to liquids and conducive to snap fit assembly.

3. The apparatus of claim 1 wherein access holes in said top plate are labeled for easy reference.

4. The apparatus of claim 1 wherein the ratio of diameter to height of said base is approximately 2:1, creating a stable storage platform during procedure.

5. The apparatus of claim 1 wherein water is added to said base increasing it stability even further.

6. A method of presenting various guidewires, and other such devices during endovascular procedures, storing said devices during such procedures and disposing of said devices and waste bodily fluids after said procedures completed comprising the steps of:
  removing coiled devices from sterile packages;
  inserting said devices through individual access holes in a top plate of a container, said container comprising a cylindrical base with a cylindrical reservoir internal and coaxial to said base, a stack of annular rings baffles each forming an annular bin between the inside diameter of said base and the outside diameter of said reservoir, topped by said top plate with said access holes positioned above access pockets to the various annular bin levels, circumferentially until only a sufficient length of said devices is protruding above the top surface of said top plate for the physician to readily grasp and remove it when ready for use in said procedure;
  withdrawing said device from said container and inserting into a patient's vascular structure;
  removing said device completely or partially from said patient and feeding the proximal portion back into said container during procedure;
  collecting waste bodily fluids that have run along guide wire devices into said reservoir;
  pushing distal ends of devices into said access holes n said top plate after procedure completed;
  snapping said sealing lid over said top plate and base, making a liquid sealed unit; and
  disposing of said sealed unit holding waste bodily fluids and used devices.

* * * * *